United States Patent [19]

Williams

[11] 4,412,081
[45] Oct. 25, 1983

[54] METHODS FOR PREPARING DECAMETHYL CYCLOPENTASILOXANE

[75] Inventor: Robert E. Williams, Scotia, N.Y.

[73] Assignee: General Electric Company, Schenectady, N.Y.

[21] Appl. No.: 412,062

[22] Filed: Aug. 27, 1982

[51] Int. Cl.$^3$ .................................................. C07F 7/08
[52] U.S. Cl. ...................................................... 556/460
[58] Field of Search ......................................... 556/460

[56] References Cited

U.S. PATENT DOCUMENTS

| | | | |
|---|---|---|---|
| 2,816,124 | 12/1957 | York | 556/460 |
| 3,465,016 | 9/1969 | Hampton | 556/460 |
| 4,197,251 | 4/1980 | Hirakawa et al. | 556/460 |
| 4,222,952 | 9/1980 | Vick | 556/460 UX |

*Primary Examiner*—Paul F. Shaver
*Attorney, Agent, or Firm*—William H. Pittman; James C. Davis, Jr.; James Magee, Jr.

[57] ABSTRACT

Decamethyl cyclopentasiloxane can be prepared in good yields by treatment of octamethylcyclotetrasiloxane with aqueous hydrochloric acid and a normal $C_{6-16}$ alkyl sulfonic acid.

5 Claims, No Drawings

METHODS FOR PREPARING DECAMETHYL CYCLOPENTASILOXANE

BACKGROUND OF THE INVENTION

This invention relates to an improved method for preparing a cyclic siloxane of the general formula:

$$[(CH_3)_2SiO]_5 \qquad \text{I}$$

(also known as "pentamer" or $D_5$) from octamethyl cyclotetrasiloxane of the formula $$[(CH_3)_2SiO]_4$$

(also known as "tetramer" or $D_4$) by treating the tetramer with a normal $C_{6-16}$ alkyl sulfonic acid having the formula $$n\text{-}C_xH_{2x+1}SO_3H \qquad \text{II}$$

where $x = 6$ to 16, inclusive
in the presence of aqueous HCl at elevated temperatures.

The term "normal $C_{6-16}$ alkylsulfonic acid" is intended to include not only the acid itself but also its negatively charged alkali metal salts thereof, for instance, the sodium salt of the sulfonic acid. For convenience, availability, and cost, the sodium salt (which is an anionic surfactant while the corresponding free sulfonic acids are nonionic surfactants) is used in the examples which are illustrative of this invention. However, essentially all the sodium salts are analogues of the sulfonic acids and are converted to the acid in the presence of the aqueous HCl. Therefore, the active catalyst is the alkyl sulfonic acid, or mixtures thereof.

Among the n-alkyl sulfonic acids which can be employed in the practice of the present invention, in addition to those recited in the following examples, may be mentioned for instance, $C_8H_{17}SO_3H$, $C_{10}H_{21}SO_3H$, $C_{12}H_{25}SO_3H$, $C_{14}H_{29}SO_3H$, $C_{16}H_{33}SO_3H$, etc. Included within the scope of these sulfonic acids are the precursor alkali-metal salts thereof, such as the sodium, potassium, etc. salts, which under the reaction conditions of carrying out the invention, are converted to the sulfonic acid.

STATEMENT OF THE INVENTION

The cyclic polysiloxane pentamer has been found to be useful in cosmetic applications, e.g., in anti-perspirant formulations, and also as a starting ingredient for making silicone oils, rubbers, and other silicone fluids. It is commercially important that in preparing the pentamer that it be in a pure form so that it can be used for its intended purpose.

In making silicone fluids, it is generally desirable to react a cyclic polysiloxane in the above category with hexamethyldisiloxane with a mineral acid so that linear polysiloxanes are formed with chain-stopped trimethylsiloxy units or any other organosiloxy units which it may be desired to insert or other chain-stoppers into the polymer chain.

The sulfonic acid is used only in small effective catalytic amounts required to give the desired results of obtaining predominantly large quantities of pentamer from the tetramer. Thus, the amount of the sulfonic acid which can be employed can vary from about 0.1% to about 2%, by weight based on the weight of the aqueous HCl. The longer alkyl chains of the sulfonic acid, although useful form emulsions and may thereby complicate separation of the desired product. The HCl concentration in the water should range from about 20% to 36% HCl or even slightly higher such as saturated aqueous HCl.

The temperature at which the reaction is carried out should be carefully monitored above 50° up to 100° C., preferably between 70° to 95° C. if increased yields of pentamer are to be realized. The mean liquid residence time of the aqueous HCl and the tetramer can be varied and is preferably of the order of about 30 minutes to 3 hours; too long a time will cause excess polymer formation.

The amount of HCl which should be employed in the reaction can be varied widely. It will depend upon such factors as the amount of sulfonic acid, (or alkali metal salt thereof) used, the time of reaction, the temperature, etc. Generally, I have found that the aqueous HCl is employed in an amount, by weight, of from 0.5 to 4 parts of the aqueous HCl per part of the tetramer. Vigorous stirring should be employed during the heating reaction in order to insure intimate contact of the reactants.

In order that those skilled in the art may better understand how the present invention can be practiced, the following example is given by way of illustration and not by way of limitation.

EXAMPLE 1

In this example, 50 grams of tetramer was added to 100 grams of 36% aqueous HCl containing 0.5 gram of the normal decylsulfonic acid sodium salt having the formula $$C_{10}H_{21}SO_3^{(-)}Na^{(+)}$$

While stirring vigorously, the mixture was heated at 90° C. for varying lengths of time and then analyzed by vapor phase chromatography to determine how much of the pentamer had been obtained from the tetramer. The following Table I shows the results of various heating times and the effect of the yield of pentamer, based on the time of heating under the conditions of reaction.

TABLE I

| Hours Reaction Time | % Tetramer | % Pentamer | [a]% Hexamer |
|---|---|---|---|
| 1 | 41 | 38 | 9 |
| 2 | 32 | 34 | 11 |
| [b]24 | 8 | 5 | 2 |

[a]$[(CH_3)_2SiO]_6$
[b]Low yields of products due to polymer formation

It is obvious from the above table, the maximum amount of pentamer is formed early in the reaction, and further heating (24 hours) under the reaction conditions recited resulted in polymer formation rather than in the more desirable pentamer formation.

EXAMPLE 2

Following the procedure of Example 1, 50 grams of tetramer was added to 100 grams of 36% aqueous HCl containing 0.2 gram $C_{10}H_{21}SO_3^{(-)}Na^{(+)}$ while stirring vigorously at 90° C. Analysis by gas chromatography gave the following results.

TABLE II

| Hours Reaction Time | % Tetramer | % Pentamer | % Hexamer |
| --- | --- | --- | --- |
| 1.0 | 71 | 17 | 2 |
| 2.0 | 59 | 30 | 5 |
| 4.0 | 40 | 34 | 7 |
| 7.0 | 31 | 33 | 8 |

EXAMPLE 3

Following the procedure of Example 1, 50 grams of tetramer was added to 100 grams of 36% aqueous HCl containing 0.2 gram $C_{12}H_{25}SO_3^{(-)}Na^{(+)}$ while stirring vigorously at 90° C. Analysis by gas chromatography gave the following results.

TABLE III

| Hours Reaction Time | % Tetramer | % Pentamer | % Hexamer |
| --- | --- | --- | --- |
| 0.5 | 56 | 20 | 3 |
| 1.0 | 47 | 31 | 5 |
| 2.0 | 32 | 33 | 8 |
| 4.0 | 23 | 28 | 8 |

EXAMPLE 4

This example shows the effect of omitting the sulfonic acid. More particularly, 50 grams tetramer was added to 100 grams of 36% aqueous HCl while stirring vigorously at 90° C. Analysis by gas chromatography gave the following results.

TABLE IV

| Hours Reaction Time | % Tetramer | % Pentamer |
| --- | --- | --- |
| 1.0 | 60 | 3 |
| 2.0 | 40 | 9 |

It will of course be understood by those skilled in the art that other sulfonic acids and alkali metal salts thereof, many examples of which have been given above, may be used in place of the decyl sulfonic acid compound of the above example, as well as the conditions for carrying out my invention, can be varied within the limits as described above to obtain the increased yields of the pentamer. Longer chain alkyl sulfonic acids tend to give better yields of the pentamer than the shorter chain alkyl sulfonic acids. The temperature can be varied within the limits described above and the times of reaction can also be varied, but care must be exercised both in temperature and in time of reaction, that they are not excessive in order to avoid undue formation of polymer which would defeat the purpose of obtaining increased yields of the pentamer. As should be evident, instead of using 36% aqueous HCl, one could employ other concentrations of aqueous HCl, such as 20% HCl with essentially equivalent results.

What I claim and desire to secure by Letters Patent of the United States is:

1. A process for preparing a cyclic pentamer siloxane of the general formula $$[(CH_3)_2SiO]_5$$

from octamethyl cyclotetrasiloxane by heating the latter with a normal $C_{6-16}$ alkyl sulfonic acid having the formula $$n\text{-}C_xH_{(2x+1)}SO_3H$$

where x=6 to 16, inclusive, in the presence of aqueous HCl at a temperature in excess of 50° C.

2. The process as in claim 1 wherein the reaction temperature is between 50°–100° C.

3. The process as in claim 1 wherein the sulfonic acid is present in an amount ranging from 0.1 to 2%, by weight, based on the weight of the aqueous HCl.

4. The process as in claim 1 wherein the alkyl sulfonic acid is n-decyl sulfonic acid.

5. The process as in claim 1 wherein the time of reaction is from about 30 minutes to 3 hours.

* * * * *